US010729453B2

(12) United States Patent
Woodard et al.

(10) Patent No.: US 10,729,453 B2
(45) Date of Patent: Aug. 4, 2020

(54) GUIDANCE SYSTEM FOR HALLUX VALGUS CORRECTION

(71) Applicant: Wright Medical Technology, Inc., Memphis, TN (US)

(72) Inventors: Joseph Ryan Woodard, Memphis, TN (US); Brian Robert Thoren, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 56 days.

(21) Appl. No.: 16/108,311

(22) Filed: Aug. 22, 2018

(65) Prior Publication Data
US 2020/0060690 A1 Feb. 27, 2020

(51) Int. Cl.
*A61B 17/15* (2006.01)
*A61B 17/16* (2006.01)
*A61B 17/56* (2006.01)

(52) U.S. Cl.
CPC ........ *A61B 17/1682* (2013.01); *A61B 17/151* (2013.01); *A61B 17/157* (2013.01); *A61B 2017/565* (2013.01)

(58) Field of Classification Search
CPC ..... A61B 17/15; A61B 17/151; A61B 17/152; A61B 17/154; A61B 17/155; A61B 17/157; A61B 17/158; A61B 17/1682; A61B 17/565; A61B 17/1775
See application file for complete search history.

(56) References Cited

U.S. PATENT DOCUMENTS

| 4,952,213 A * | 8/1990 | Bowman | A61B 17/157 606/62 |
| 5,662,656 A * | 9/1997 | White | A61B 17/155 606/86 R |
| 2005/0143746 A1* | 6/2005 | Steffensmeier | A61B 17/154 606/88 |
| 2007/0265634 A1* | 11/2007 | Weinstein | A61B 17/15 606/87 |
| 2011/0319901 A1 | 12/2011 | Birkbeck et al. | |
| 2016/0192950 A1 | 7/2016 | Dayton et al. | |
| 2016/0235414 A1 | 8/2016 | Hatch et al. | |
| 2016/0310191 A1* | 10/2016 | Seykora | A61B 17/1764 |

OTHER PUBLICATIONS

International Search Report and Written Opinion issued in connection with corresponding International Patent Application No. PCT/US2019/038686, dated Sep. 13, 2019, 8 pages.

* cited by examiner

*Primary Examiner* — Christian A Sevilla
(74) *Attorney, Agent, or Firm* — Duane Morris LLP

(57) ABSTRACT

A guidance system comprises a first guide configured to be detachably mounted to a first portion of a bone. The first guide has a first axis for alignment with a longitudinal axis of the first portion of the bone. A second guide is mountable on the first guide. The second guide is slidably translatable in a transverse direction relative to the first axis. A third guide is mountable on the second guide. The third guide is selectively positionable along a curved path extending at least part way around the longitudinal axis.

11 Claims, 17 Drawing Sheets

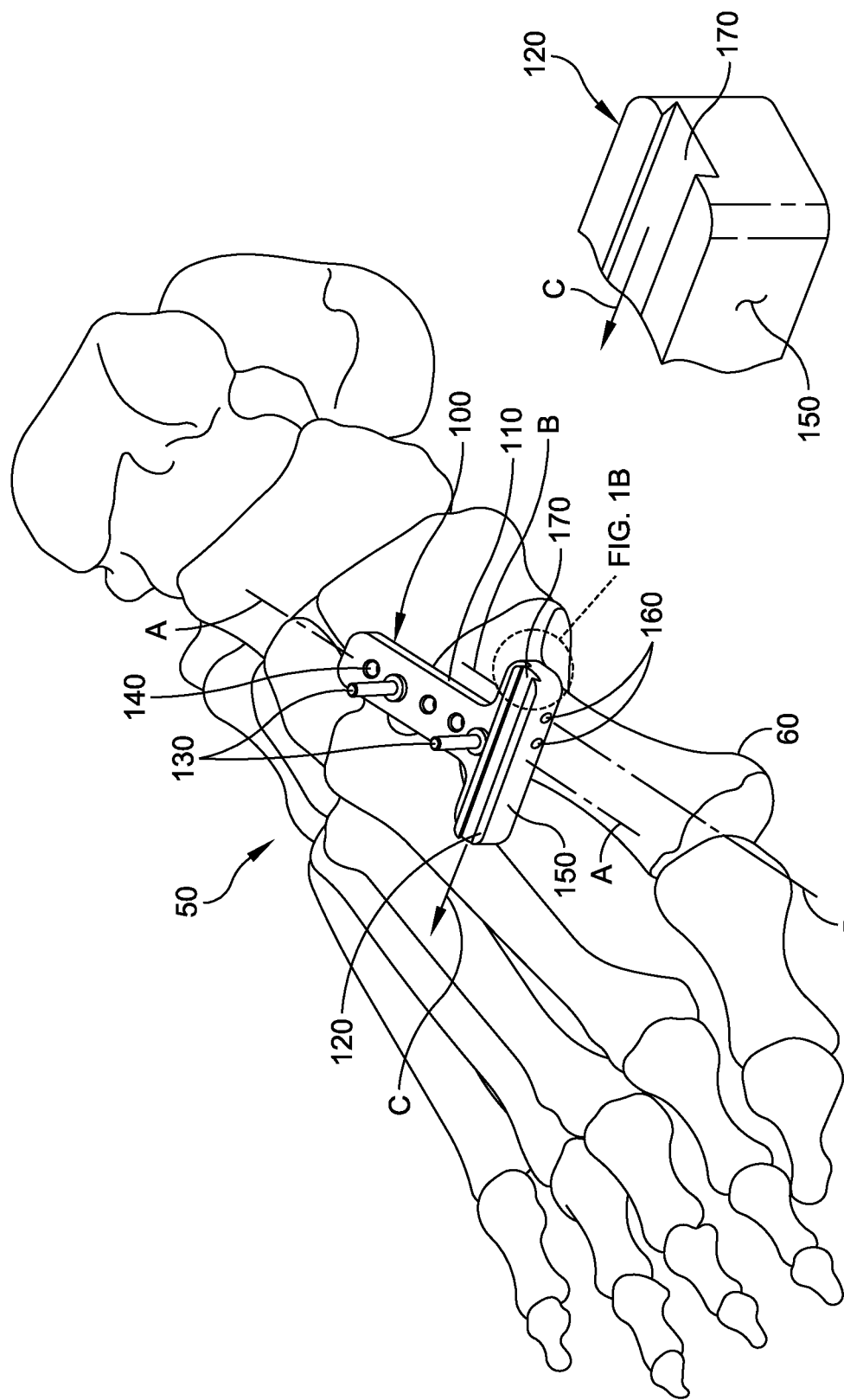

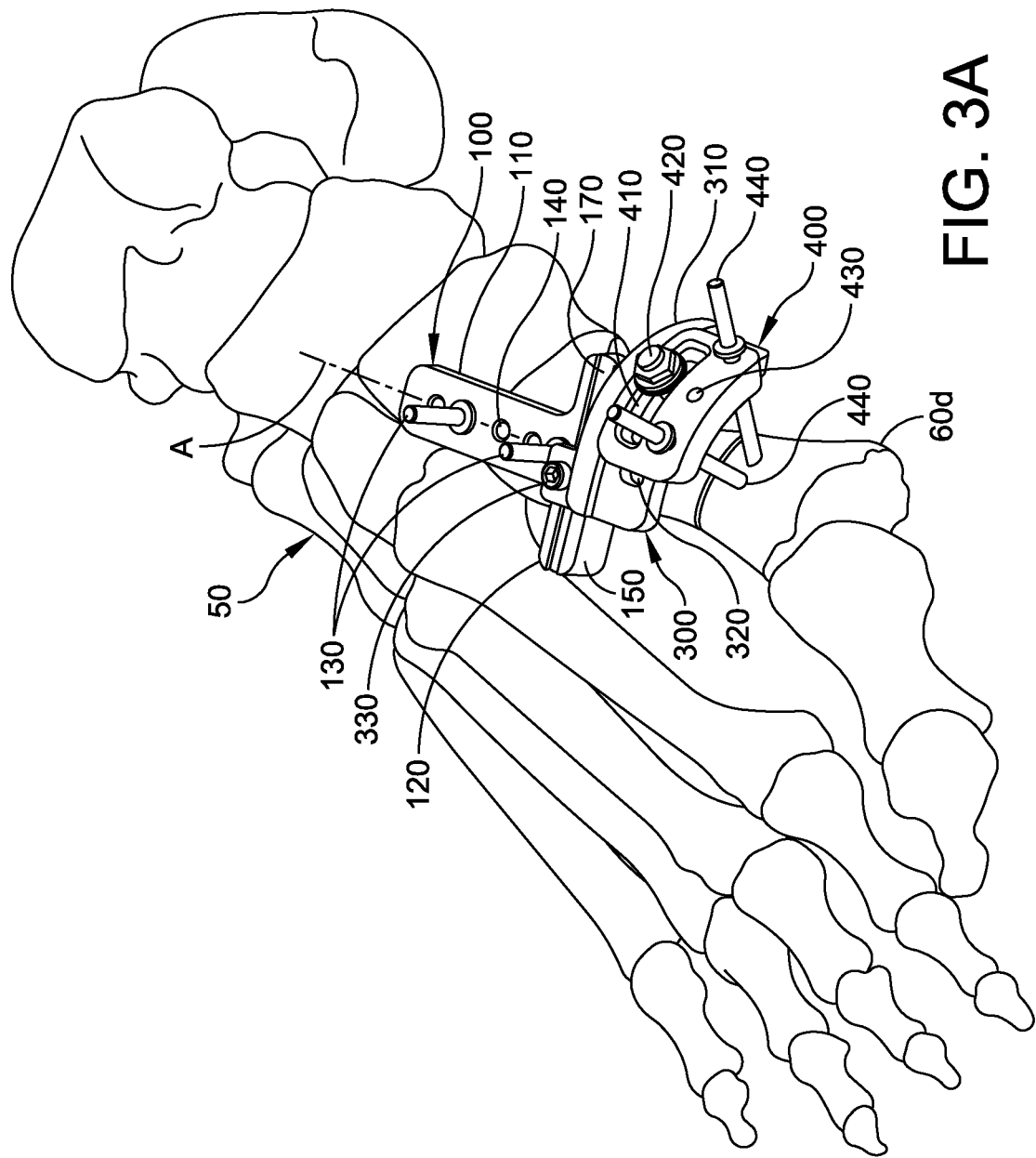

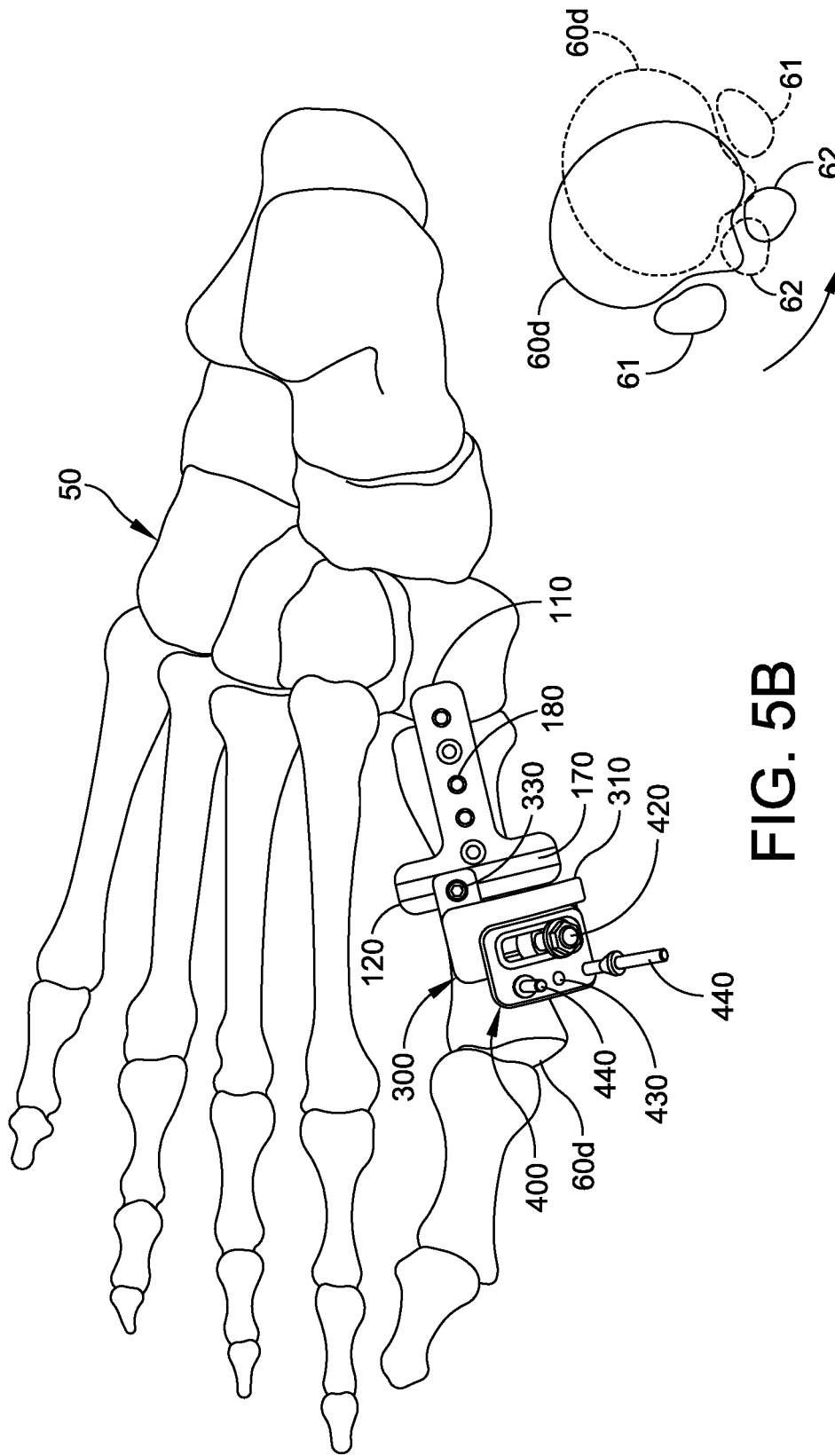

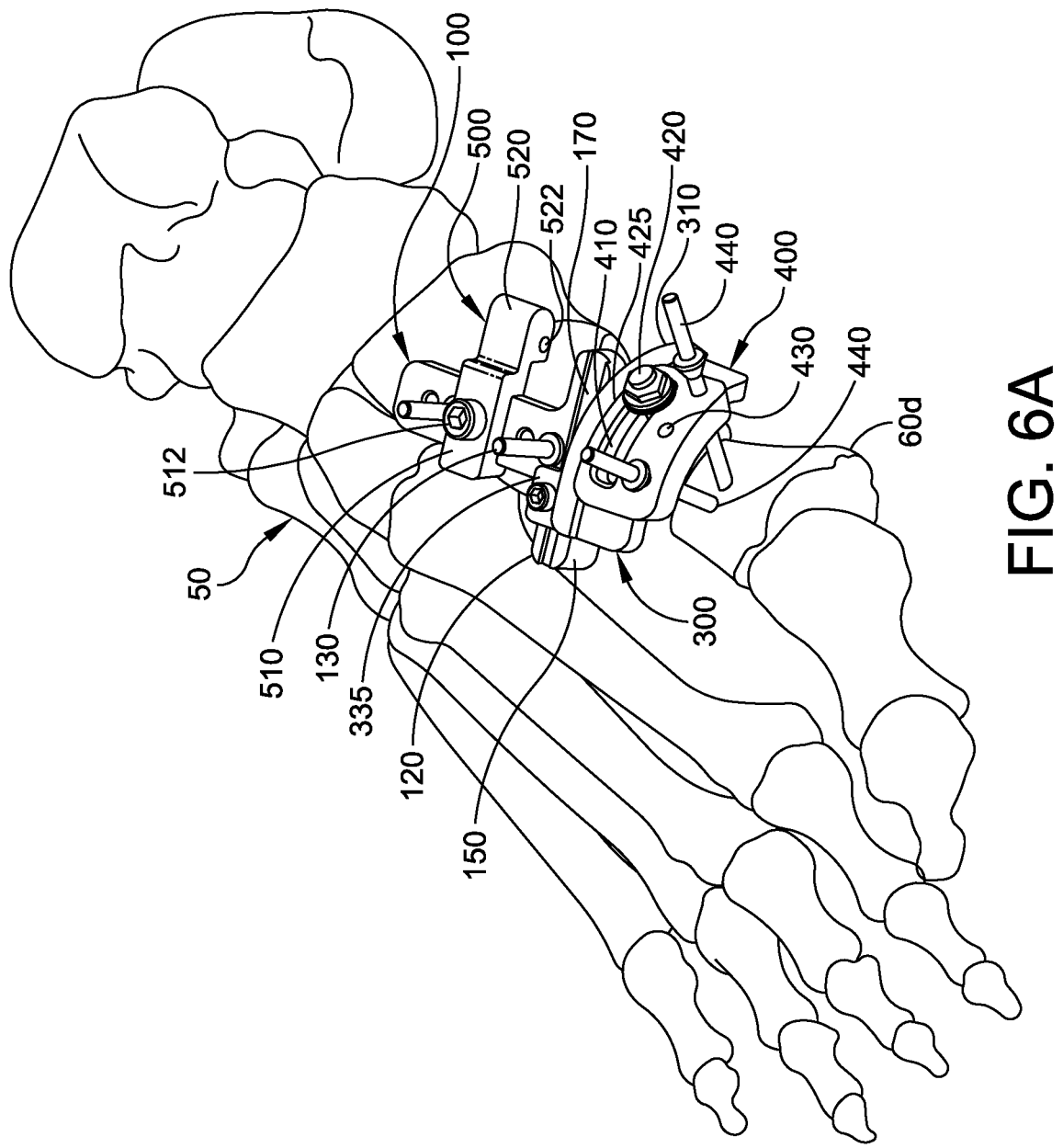

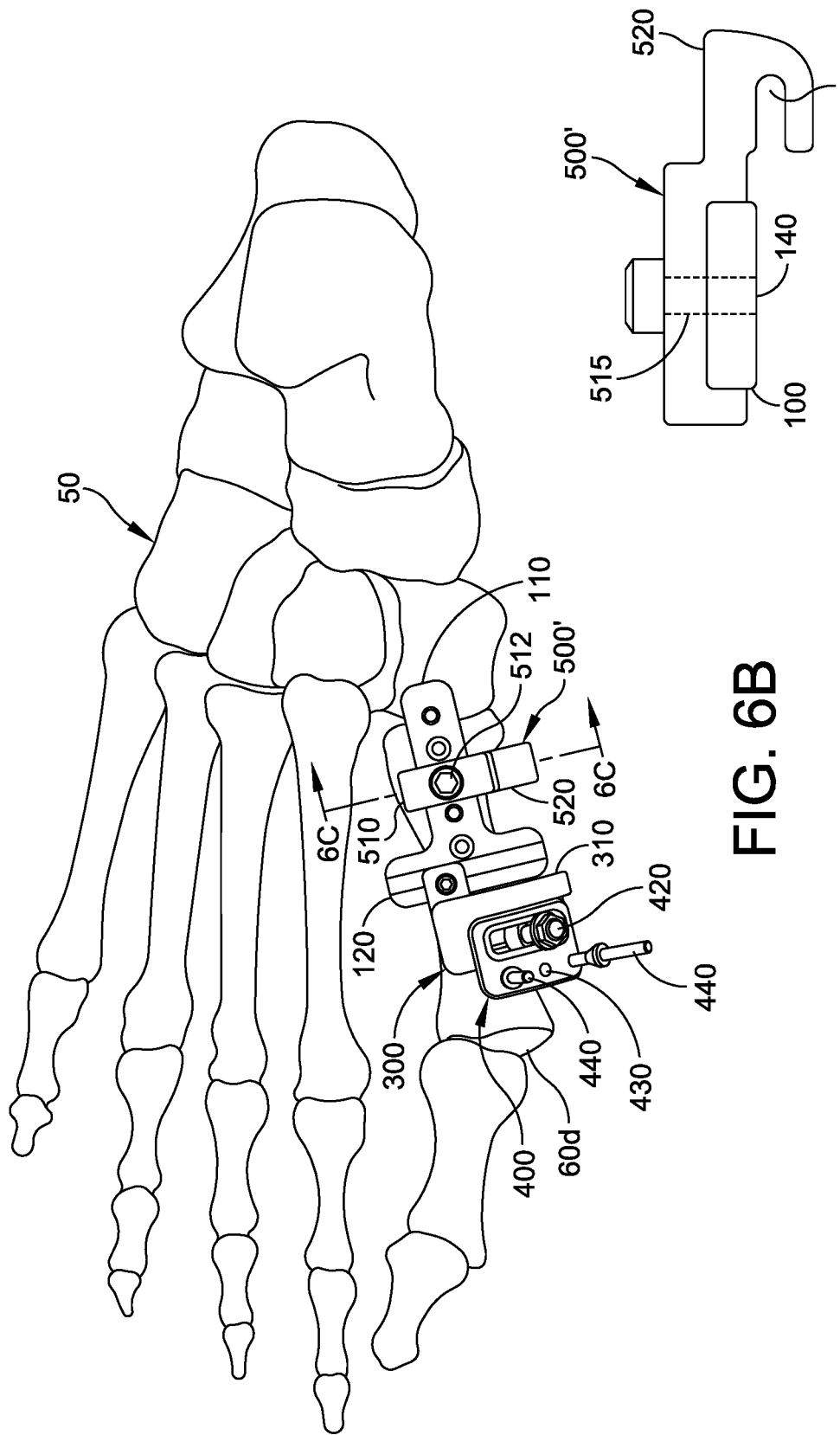

GUIDANCE SYSTEM FOR HALLUX VALGUS CORRECTION

FIELD

This disclosure relates generally to medical devices, and more specifically to guidance systems for correcting bone deformities.

BACKGROUND

A bunion deformity (hallux valgus) is caused by a medial deviation of the first metatarsal and lateral deviation of the great toe (hallux). Distal osteotomies of the first metatarsal are commonly performed to correct hallux valgus. During the surgery, the surgeon cuts the first metatarsal along a plane that is transverse to the longitudinal axis of the first metatarsal, dividing the bone into a proximal portion (adjacent the medial cuneiform bone) and a distal portion (adjacent the first proximal phalanx). The distal portion is translated in the lateral direction relative to the proximal portion, and the translated distal portion is fixed in place (using an implant and/or one or more fixation elements (e.g., screws, k-wires or rods). In some patients, in addition to the lateral deviation of the first metatarsal, the medial (tibial) and lateral (fibular) sesamoid bones of the first metatarsal are displaced. These sesamoid bones are embedded within the medial and lateral heads of the flexor halluces brevis tendons adjacent to the plantar surface of the first metatarsal. In the case of hallux valgus, the sesamoid bones may be displaced from the plantar side of the first metatarsal toward the lateral side of the first metatarsal.

SUMMARY

In some embodiments, a guidance system comprises a first guide configured to be detachably mounted to a first portion of a bone. The first guide has a first axis for alignment with a longitudinal axis of the first portion of the bone. A second guide is mountable on the first guide. The second guide is slidably translatable in a transverse direction relative to the first axis. A third guide is mountable on the second guide. The third guide is selectively positionable along a curved path extending at least part way around the longitudinal axis.

In some embodiments, a method for using a guidance system comprises: fixing a first guide to a bone; cutting the bone to provide a first bone portion and a second bone portion, the first bone portion having a first longitudinal axis; placing a second guide at a selected position relative to the first guide along a transverse direction normal to the first longitudinal axis; and moving a third guide around the longitudinal axis to rotate the second portion of the bone to a target angle relative to the first portion of the bone.

BRIEF DESCRIPTION OF THE DRAWINGS

FIG. 1A is an isometric view of a first guide on a foot.
FIG. 1B is an enlarged detail of FIG. 1A.
FIG. 3A is an isometric view of the first guide, a second guide, and a third guide on the foot.
FIG. 5B is a dorsal view of the foot and guidance system after rotating the third guide around the second guide and distal portion of the bone.
FIG. 5C is an anterior view of the distal end of the first metatarsal, before rotation (in solid lines) and after rotation (in phantom).
FIG. 6A shows the guidance system with the fourth guide attached to the first guide.
FIG. 6B is a dorsal view of the guidance system with a variation of the fourth guide attached to the first guide.
FIG. 6C is a cross-sectional view of the guidance system taken along section line 6C-6C of FIG. 6B.

DETAILED DESCRIPTION

Figure 1C:
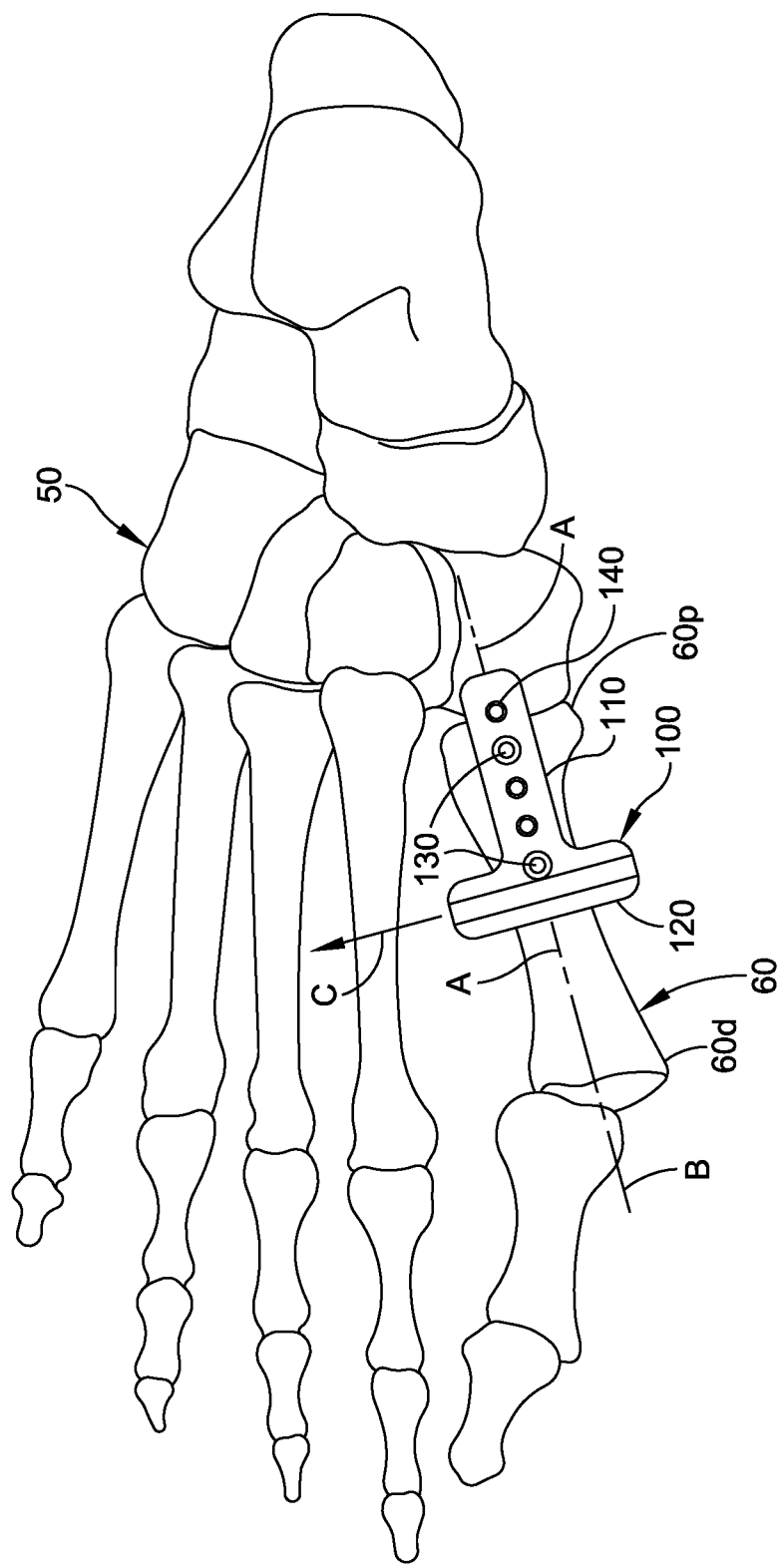
FIG. 1C is a dorsal view of the foot with the first guide.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

In the examples described below, the guidance system is used for a corrective surgery for hallux valgus. The examples herein refer to correction of the first metatarsal. In other embodiments—detailed description of which are omitted solely for brevity—the guidance system is used for correction of deformities in other bones, where the correction can include a translation and/or a rotation of a second portion of the bone with respect to a first portion of the bone.

This disclosure provides a guidance system for use during hallux valgus corrective surgery. The guidance system allows the surgeon to translate the distal portion of the first metatarsal in the lateral direction and rotate the distal portion about the longitudinal axis of the distal portion, to position the sesamoid bones in the proper (plantar) location.

Referring to FIG. 6A, in some embodiments, a guidance system comprises a first guide 100 (FIG. 1A) configured to be detachably mounted to a first (proximal) portion 60p of a bone 60. The first guide 100 has a first axis A for alignment with a longitudinal axis B of the first portion 60p of the bone 60. The first guide 100 can be fixed to the first metatarsal 60 using one or more fixation elements (e.g., k-wires, screws, rods, straps, clamps or the like) to provide reference surfaces for a second guide 300.

The second guide 300 is mountable on the first guide 100. The second guide 300 is slidably translatable in a transverse direction relative to the first axis A, to translate the distal portion 60d of the bone 60 relative to the proximal portion 60p.

A third guide 400 is mountable on the second guide 300. The third guide 400 is selectively positionable along a curved path extending at least part way around the longitudinal axis B of the distal portion 60d of the bone 60. In some embodiments, the third guide 400 is slidably mounted on the second guide 300, and the third guide 400 is pinned to the distal portion 60d of the bone 60. Sliding the third guide 400 along the curved path results in rotation of the distal portion 60d of the bone 60 about the longitudinal axis B of the distal portion 60d.

Some embodiments further comprise a fourth guide 500 attachable to the first guide 100. The fourth guide 500 defines an aperture 522 (FIG. 6A) or slot 524 (FIG. 6C) for receiving a fixation element 550 aligned with the second portion 60d of the bone 60. For example, a k-wire, olive wire, or nail 550 can be passed through the aperture 522 and can enter the proximal portion 60p and distal portion 60d of the bone 60.

Some embodiments further comprise a cut guide 200 (FIG. 2A) attachable to the first guide 100. The cut guide 200 has a slot 210 for receiving a cutting tool (not shown), such as a burr or blade, for separating the second (distal) portion 60d of the bone 60 from the first (proximal) portion 60p of the bone 60.

Details of the guidance system components and their use are described below.

FIGS. 1A-1C show the alignment and fixation of the first guide 100 on the foot 50 of a patient. The first guide 100 is configured to be detachably mounted to a first portion 60p of a bone 60, such as the first metatarsal or other long bone. The first guide 100 has a first member 110 with a first axis A for alignment with a longitudinal axis B of the bone 60. The first member 110 has a plurality of alignment apertures 140 extending through the first member 110, from a proximal face to a distal face (where the proximal face is adjacent to the dorsal surface of the foot). The alignment apertures 140 are configured to receive fixation elements 130 (e.g., k-wires, olive wires, screws, or the like). Although the exemplary first member 110 has five apertures 140, other embodiments can include any desired number of apertures.

The first guide 100 has a second member 120, which can be perpendicular to the first member 110. The second member 120 has a first planar surface 150 perpendicular to the first axis A of the first member 110. For example, the first guide 100 can be a T-shaped structure having a vertical (first) member 110 containing the apertures 140 for receiving fixation elements 130 and a horizontal (second) member 120 having a planar surface, rail or channel 170. As shown in the detail of FIG. 1B, the surface, rail or channel 170 can be a dovetail channel 170 or a vertical-walled (right angle) channel facing away from the dorsal surface of the foot 50. The horizontal member 120 of the first guide 100 has a transverse edge 150 configured to face away from the proximal portion 60p of the bone 60.

The transverse edge 150 lies along a plane that is orthogonal to the longitudinal axis A of the vertical portion 110. of the first (proximal) portion 60p of the bone 60. In some embodiments, the transverse edge 150 has two mounting holes 160 (FIG. 1A) to receive corresponding alignment pins (not shown in FIG. 1A) of the cut guide 200 (FIGS. 2A and 2B).

The surgeon can fix the first guide 100 to the first metatarsal 60 using two of the fixation elements 130 in two of the alignment apertures 140. The surgeon can select two of the alignment apertures 140 based on local bone quality to ensure reliable positioning. The first guide 100 is positioned along the length of the bone 60 so that the distance between the transverse edge 150 and the distal end of the bone 60 is large enough to accommodate the second guide 300 and the third guide 400. Additionally, the first guide 100 is positioned along the length of the bone 60 so that the distance between the transverse edge 150 and the distal end of the bone 60 is at least large enough to accommodate the cut guide 200. In some embodiments (not shown), the second member 120 has a positioning groove or protuberance (not shown), which the surgeon can align (under fluoroscopy) with the first tarsometatarsal (TMT) joint. Two fixation elements 130 are inserted through the alignment apertures 140.

Figure 2A:
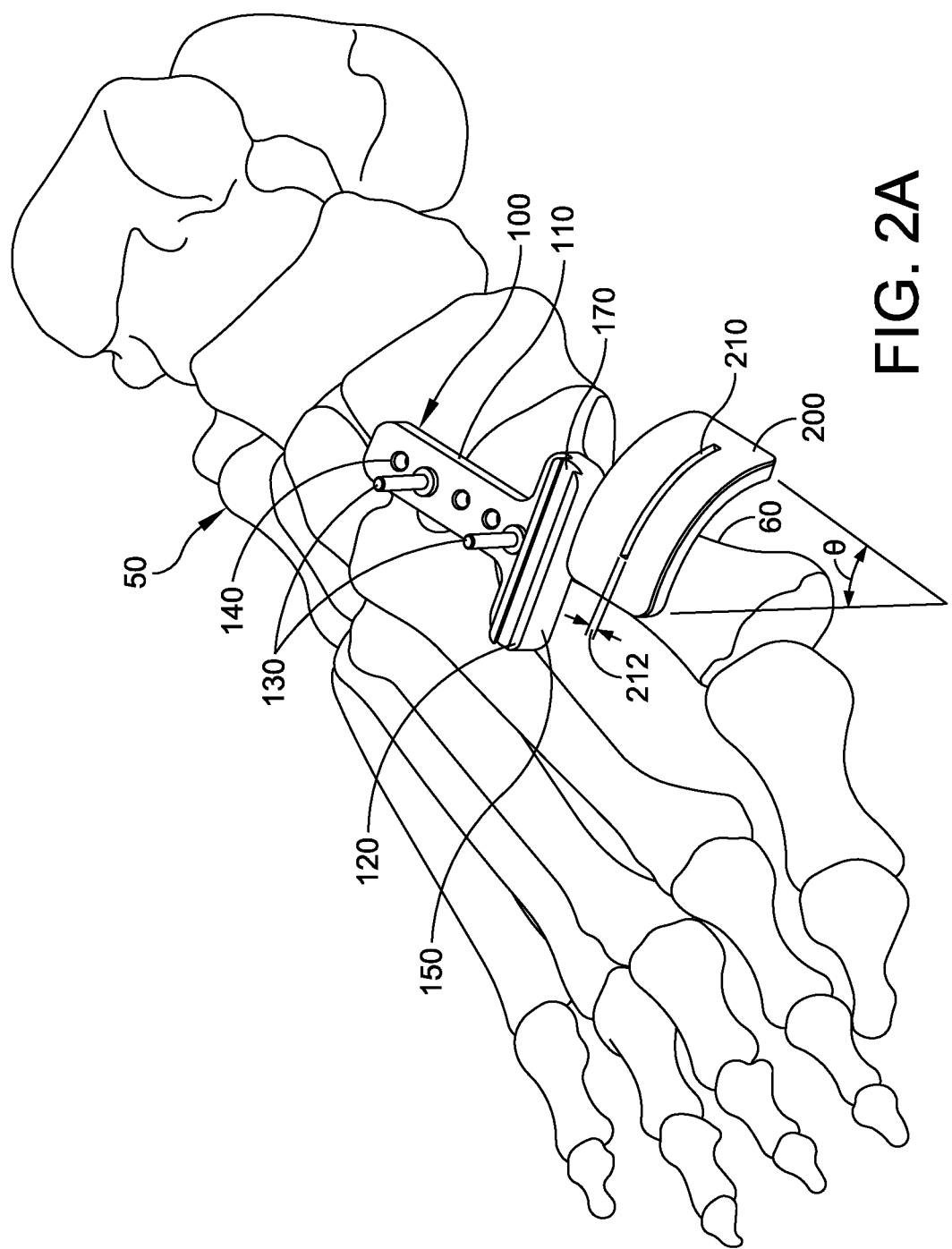
FIG. 2A is an isometric view of the foot and first guide, with a cut guide attached.
Figure 2B:
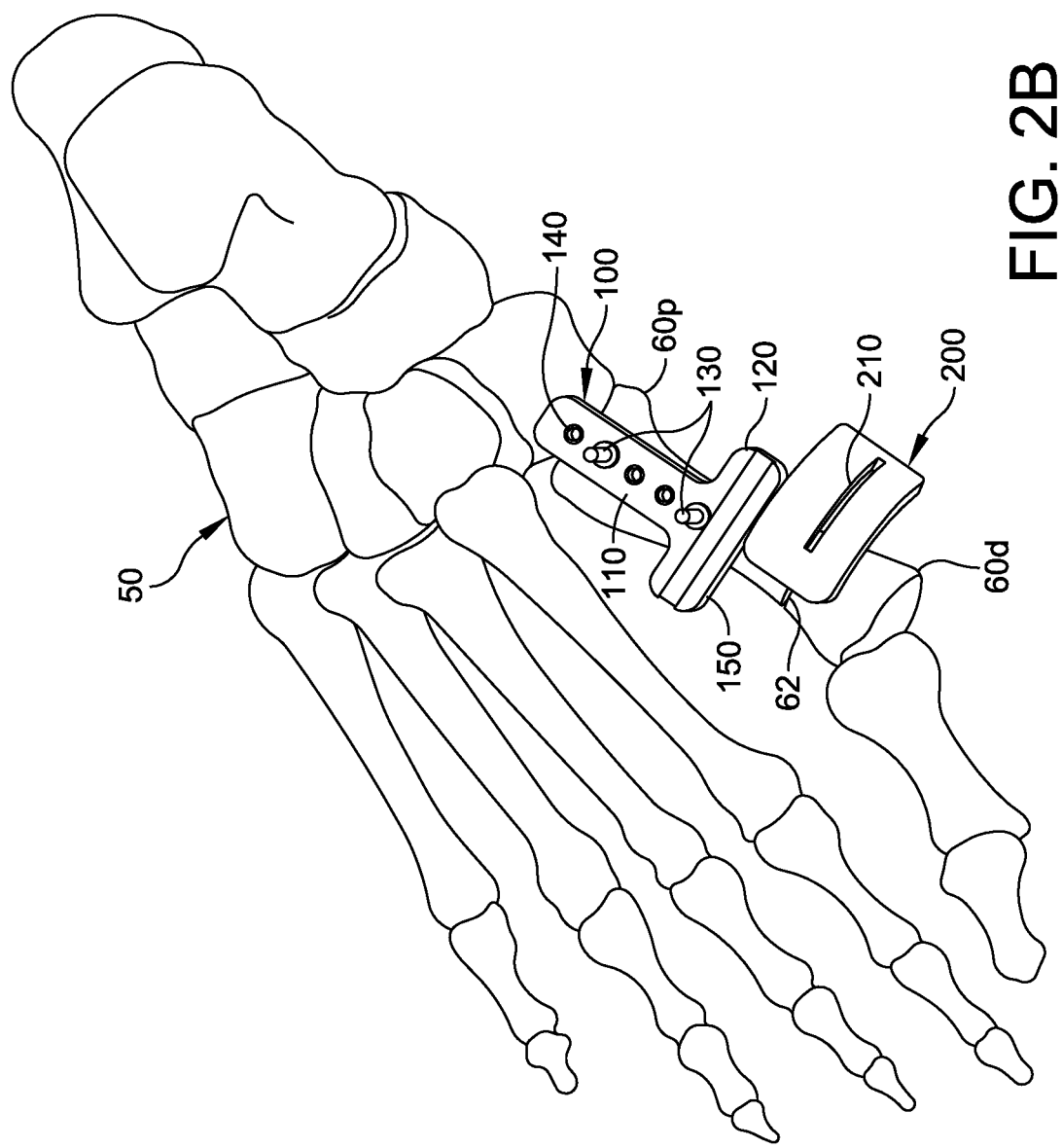
FIG. 2B is a dorsal view of the foot, first guide and cut guide of FIG. 2A.

FIGS. 2A and 2B show the cut guide 200 joined to the first guide 100. In some embodiments, the cut guide 200 has two alignment pins (not shown) configured to fit snugly into the two mounting holes 160. In other embodiments, the first guide 100 has pins (not shown) protruding from the transverse edge 150, and the cut guide 200 has corresponding holes (not shown) positioned to receive the pins. In other embodiments, one of the transverse edge 150 or the cut guide 200 has a channel or rail, and the other one of the transverse edge 150 or the cut guide 200 has a mating rail or channel. The cut guide 200 has a slot 210 having a width 212 wide enough to receive a cutting tool (e.g., a burr or blade, not shown). The slot 210 can be longer than a diameter of the bone 60 to be cut. In some embodiments, the cut guide 200 has a curved shape subtending an arc angle Θ. In some embodiments, the surgeon selects the cut guide from a plurality of cut guides having different cut angles, allowing the surgeon to select a chevron or transverse osteotomy.

With the cut guide 200 attached to the first guide, the surgeon can insert a cutting tool (e.g., a burr or a blade, not shown) into the slot 210 of the cut guide 200 and sweep the cutting tool through the bone to form a cut 62. Thus, the cut 62 separates the bone 60 into a proximal portion 60p and a distal portion 60d, as shown in FIG. 2B. Once the cut 62 is completed, the cut guide 200 is removed from the first guide 100. The surgeon can hold the distal portion 60d of the bone 60 in position by hand at this time.

Figure 3B:
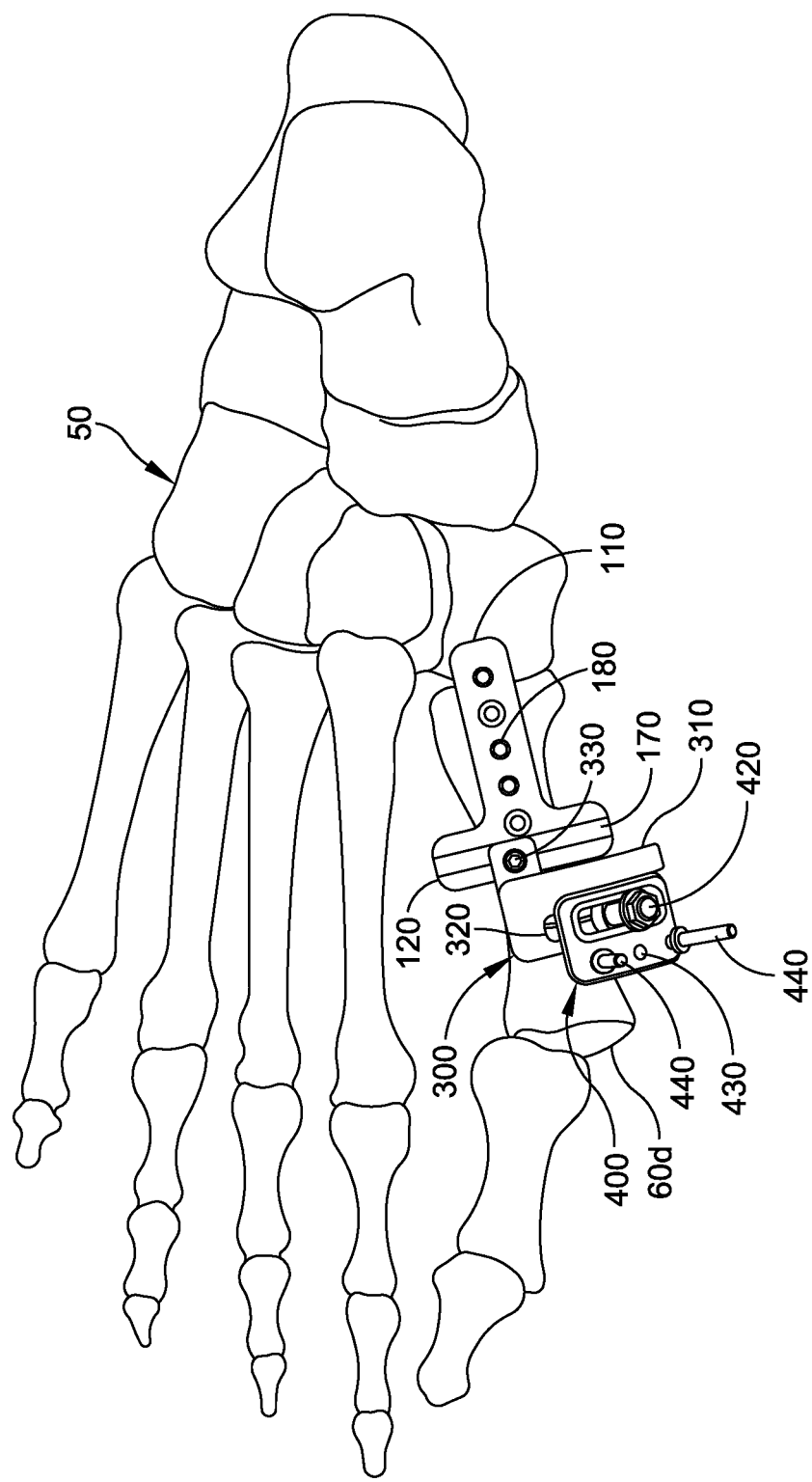
FIG. 3B is a dorsal view of the first guide, second guide and third guide.

FIGS. 3A and 3B show the second guide 300 and the third guide 400 attached to the first guide 100. FIG. 3C shows the second guide 300. The second guide 300 has a mount 335, which can include a screw-receiving hole 340. A set screw or ball plunger 330 (FIG. 3A) locks the second guide 300 in a desired medial-lateral position relative to the first guide 100. The mount 335 of the second guide 300 is configured with a channel or rail (not shown in FIG. 3C) on its plantar side complementary to the rail or channel 170 of the first guide. When the channel or rail of the second guide 300 engages the rail or channel 170 of the first guide, a second planar surface (proximal edge) 310 of the second guide 300 abuts the first planar surface (distal surface) 150 of the first guide 100. The second planar surface (proximal edge) 310 of second guide 300 is arranged to slide in the transverse direction relative to the first planar surface 150 of first guide 100. The second guide 300 also has a surface 325 which can engage and guide an abutting edge 425 (FIG. 3D) on the third guide 400.

The second guide 300 also has at least one slot or hole 320 for receiving a locking member 420 (FIG. 3A) for locking the position of the third guide 400 relative to the second guide 300. The locking member 420 can be a set screw, a screw, a bolt, a ball plunger, or the like. In some embodiments, the locking member 420 locks the third guide 400 in position on the second guide 300, without contacting the bone 60.

The exemplary second guide 300 has a curved plate 315 with a curved surface defining the slot 320. When the mount 335 of the second guide 300 engages the rail or channel 170 of the first guide 100, the curved plate 315 wraps part way around the bone 60.

Figure 3D:
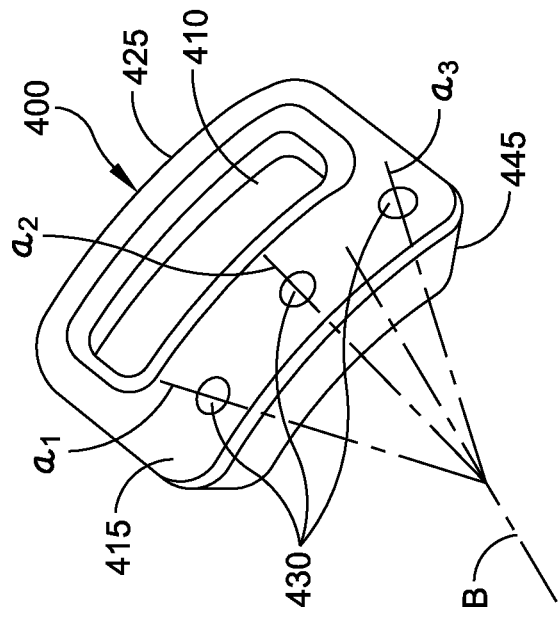
FIG. 3D is an isometric view of the third guide of FIG. 3A.
Figure 3C:
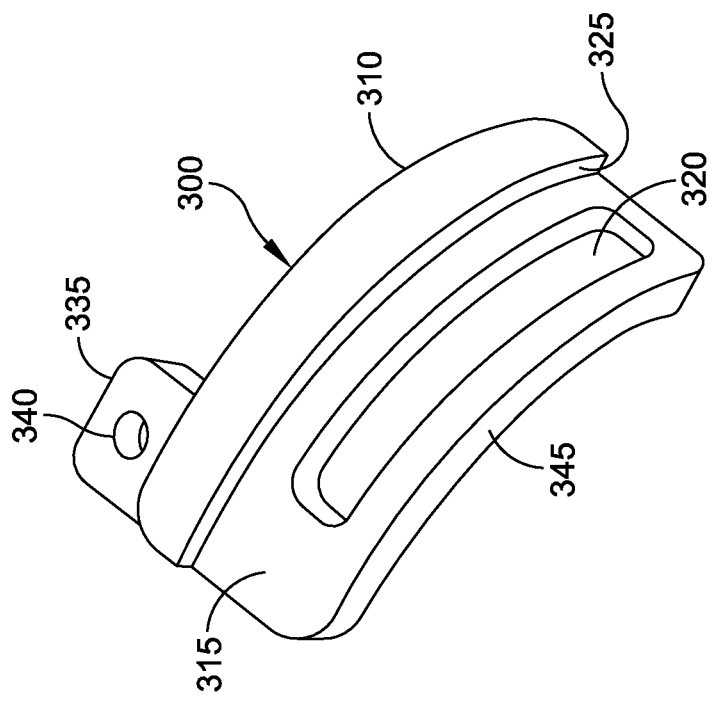
FIG. 3C is an isometric view of the second guide of FIG. 3A.

FIG. 3D shows the third guide 400. The third guide 400 is configured to be slidably mounted on the second guide 300, so the third guide 400 can move through a path that tracks the curvature of the second guide 300. Thus, when the third guide 400 slides (or revolves) relative to the second guide 300, the third guide follows a curved (e.g., circular, elliptical, or parabolic) path around the bone 60. In some embodiments, the second guide 300 and third guide 400 are both circular, and the third guide 400 has a larger radius of curvature than the second guide 300, for moving in a tangential direction within a cylindrical polar coordinate system.

The third guide 400 has at least one slot or hole 410 for receiving the locking member 420 (FIG. 3A) for locking the position of the third guide 400 relative to the second guide 300. In some embodiments, the second guide 300 has at least one round hole for fixedly locating the locking member 420, and the third guide 400 moves relative to the locking member 420. In other embodiments, the second guide 300 has plural round holes or a slot for adjustably locating the locking member 420, and the third guide 400 moves relative to the adjusted location of the locking member 420.

The third guide 400 can have additional surfaces and/or edges for engaging the second guide 300 and aligning the third guide 400 with the second guide 300. For example, the abutting edge 425 of the third guide 400 slidably abuts the surface 325 of the second guide 300. Also, the third guide 400 has a ridge 445 with a surface (not shown) that engages the edge 345 of the second guide.

The third guide 400 has at least one aperture 430 for receiving fixation members 440, such as k-wires, olive wires, rods or screws. The fixation members 440 pass through the apertures 430 of the third guide 400 and enter the bone 60. In some embodiments, the apertures 430 can be oriented toward the center of curvature of the plate 415.

For example, as shown in FIG. 3D, the third guide 400 can have a cross section with a constant radius of curvature, with the apertures 430 oriented so the fixation elements 440 passing through the apertures 430 lie along radial lines $a_1$, $a_2$, and $a_3$ which converge at a point along the longitudinal axis B of the bone 60. In this configuration, when the third guide 400 slides (or revolves) relative to the second guide 300, the third guide 400 moves in a tangential direction and traces an arc of a circle having its center point at the center of the bone 60. In some embodiments, the slot 410 of third guide 400 subtends a sufficient angle to trace through an arc of 45 degrees. In other embodiments, the slot 410 of third guide 400 subtends a sufficient angle to trace through an arc of 60 degrees. In other embodiments, the third guide 400 and its slot 410 can be configured to subtend other arcs (e.g., 90 degrees). Relative to the lock 420, the third guide 400 can be adjusted by any angle from zero to the angle of the arc subtended by the plate 415.

In preparation for surgery, the third guide 400 is preassembled to the second guide 300 and the locking member 420 is tightened. The third guide 400 is positioned relative to the locking member 420 to allow the third guide 400 to slide (or revolve) over the second guide 300 and subtend a sufficient angle of rotation to rotate the sesamoid bones to the plantar position. For example, if the sesamoid bones are displaced by 45 degrees from the plantar position (towards the lateral side), the third guide 400 is positioned with the end of slot 410 far enough from the locking member 420 to allow at least a 45 degree rotation of the distal portion 60d of bone 60 to reposition the sesamoids in the plantar position. The lock 420 is used to lock the third guide 400 relative to the second guide 300. For example, if the lock 420 is a screw, the screw 420 is tightened.

The rail (not shown) on the mount 335 of the second guide 200 is inserted in the channel 170 of the first guide 100. The (second and third guide) subassembly 300, 400 is translated laterally along the channel 170, so that the plate 415 of the third guide 400 is approximately concentric with the bone 60. That is, the subassembly (second guide 300 and third guide 400) is positioned so the center of curvature of the third guide 400 coincides with the central longitudinal axis B of the distal portion 60d of bone 60. The surgeon can adjust the position of the third guide 400 relative to the second guide 300, if appropriate, to allow a desired range of adjustment of the third guide 400. When the subassembly 300, 400 is in this concentric position, the surgeon uses the set screw or ball plunger 330 (FIG. 3A) to lock the second guide 300 in a desired medial-lateral position relative to the first guide 100.

Fixation elements (e.g., k-wires) 440 are inserted through at least one of the apertures 430 of the third guide 400 and into the distal portion 60d of the bone 60. In FIG. 3A, two fixation elements (e.g., k-wires) 440 are inserted, for example. With the third guide 400 positioned so the center of curvature of the third guide 400 coincides with the central longitudinal axis B of the bone 60, the apertures 430 align the fixation elements 440 with radial lines emanating from the central longitudinal axis B of the bone 60.

Figure 4A:
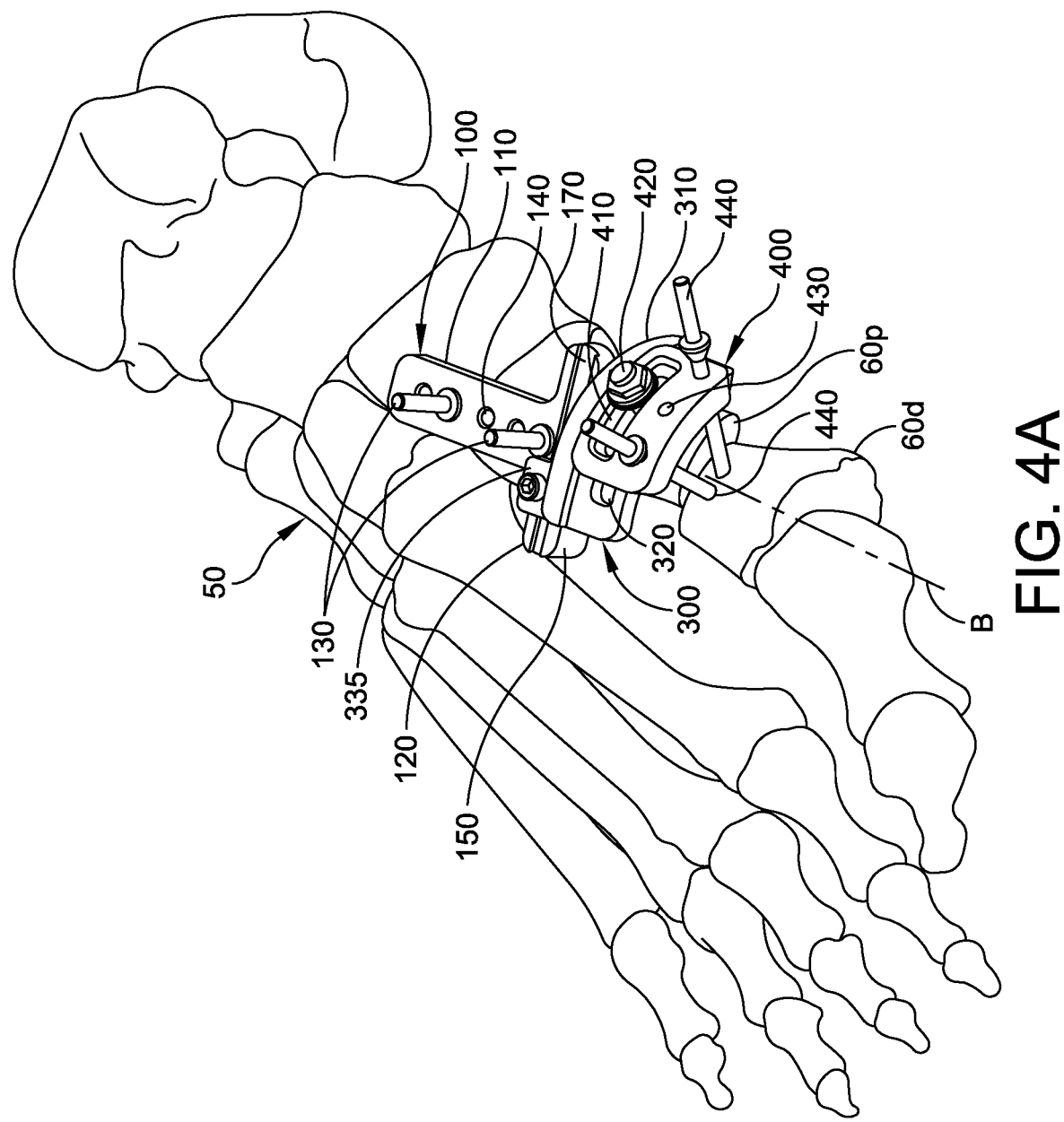
FIG. 4A is an isometric view showing the foot and guidance system after translating the second guide along the first guide.
Figure 4B:
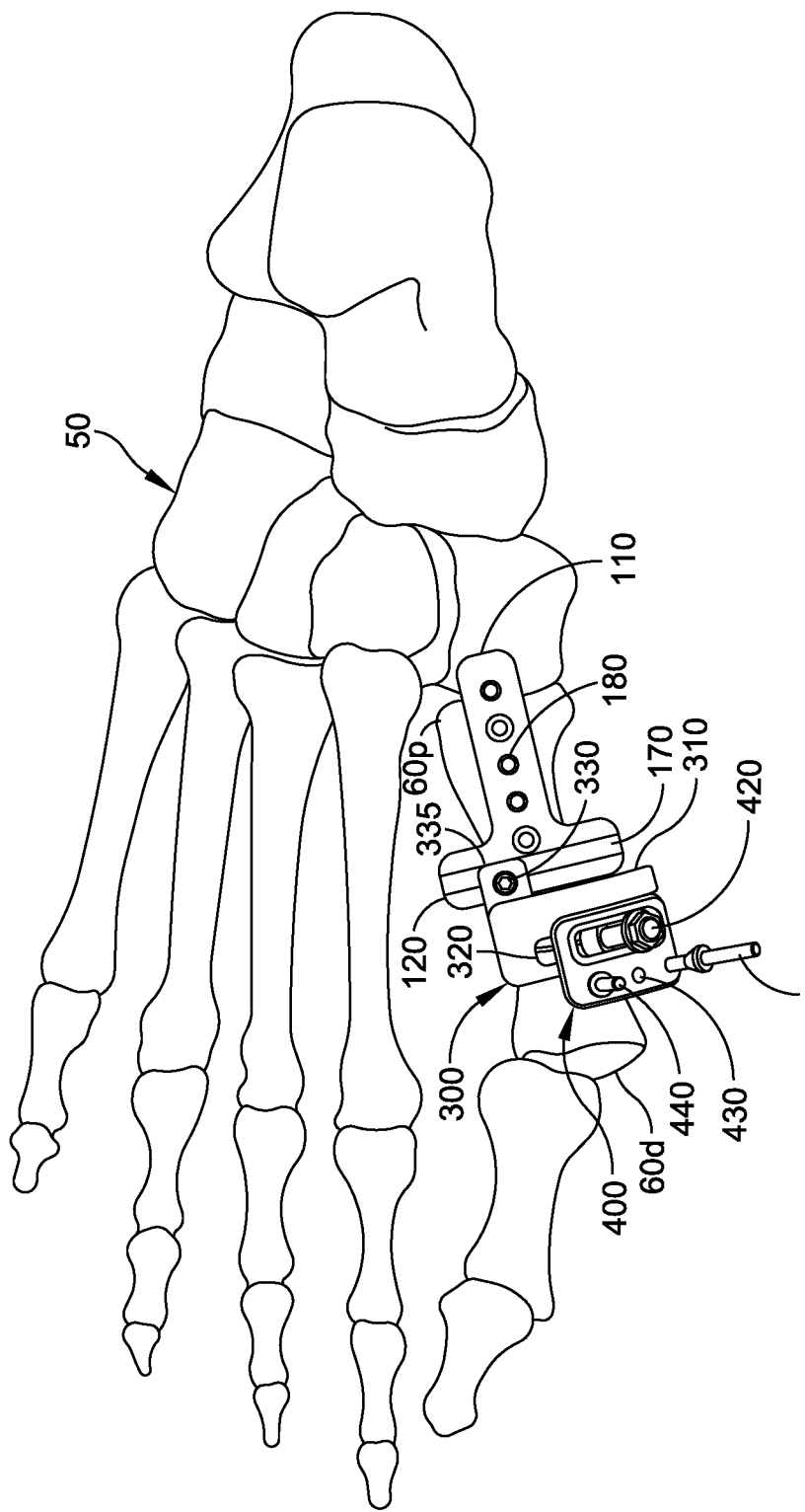
FIG. 4B is a dorsal view of the foot and guidance system after translating the second guide along the first guide.

FIGS. 4A and 4B show the translation of the distal portion 60d of the bone 60 in the lateral direction, relative to the proximal portion 60p. Once the fixation elements 440 are inserted in the distal portion 60d of bone 60, the set screw or ball plunger 330 is backed off sufficiently to allow the mount 335 to slide along the rail or channel 170 of the first guide 100. The surgeon translates the distal portion 60d of the bone 60 laterally by a sufficient offset to correct the medial deviation of the bone 60. When the desired lateral offset is achieved, the surgeon tightens the set screw or ball plunger 330 to lock in the lateral offset.

Figure 5A:
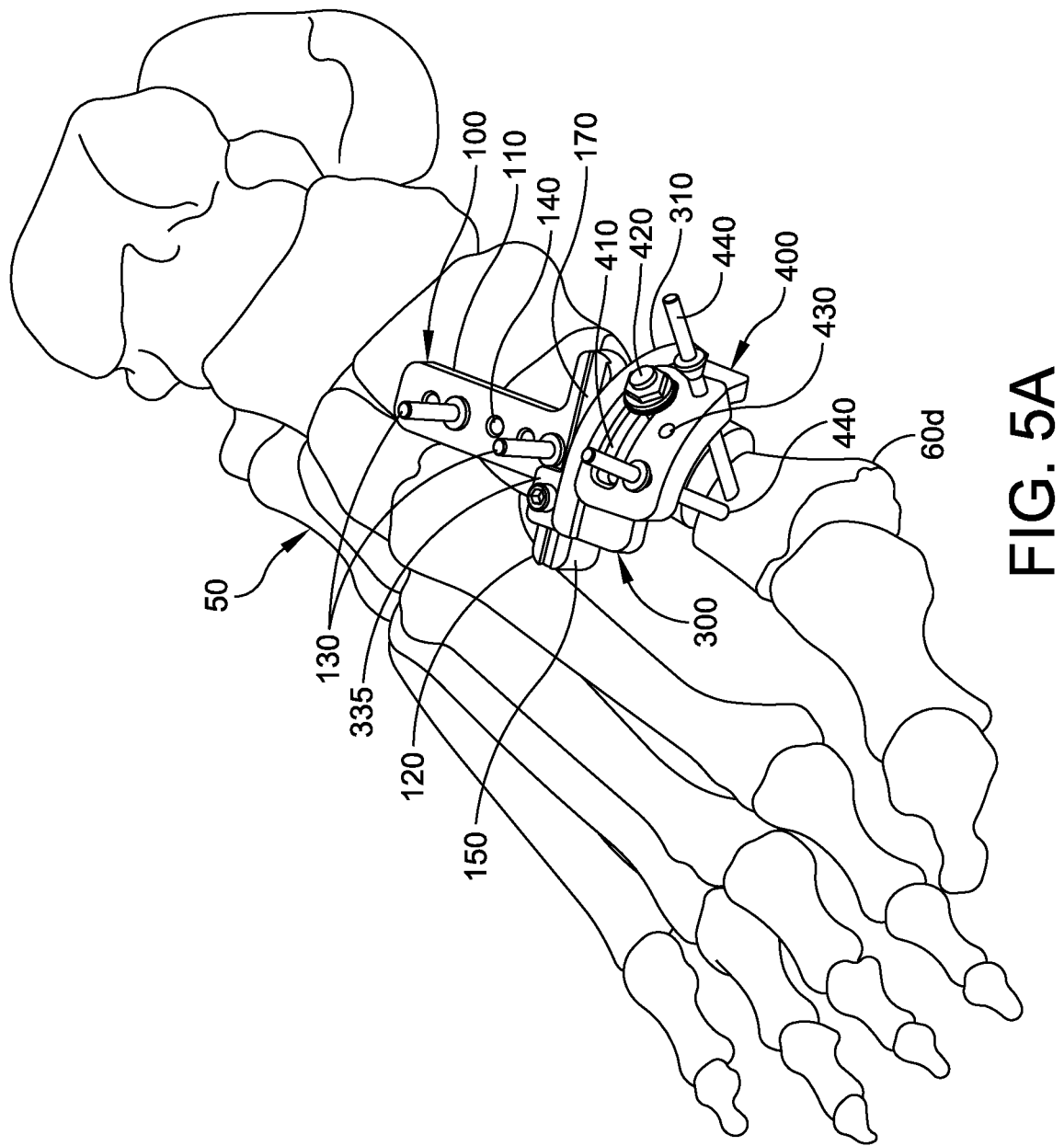
FIG. 5A is an isometric view showing the foot and guidance system after rotating the third guide around the second guide and distal portion of the bone.

FIGS. 5A-5C show the axial rotation correction of the distal portion 60d of the bone 60. With the set screw or plunger 330 locking the second guide 300 in position, the lock (e.g., threaded post or a spring loaded device) 420 is loosened to allow the third guide 400 to slide (or revolve) in a curved path over the second guide 300. Thus, the third guide 400 subtends an arc around the longitudinal center of the distal portion 60d of the bone 60, rotating the distal portion 60d about its axis B. As best seen in FIG. 5C, the distal portion 60d is rotated about its axis without translation. As shown in solid lines in FIG. 5C, the deviation of the bone 60 causes the sesamoids 61, 62 to deviate towards the lateral direction. By moving the third guide 400 through its curved path over the second guide 300, the distal portion 60d is rotated until the sesamoids 61, 62 face in the plantar direction, as shown in phantom. When the desired rotation is achieved (and the sesamoids 61, 62 face the plantar direction), the lock 420 is again tightened to lock the third guide 400 relative to the second guide 300, and fix the relative rotation of bone portions 60p, 60d.

FIGS. 6A and 6B show attachment of the fourth guide 500 to the first guide 100. FIG. 6C is a cross sectional view of the fourth guide 500, taken along section line 6C-6C in FIG. 6B. FIG. 6A shows a fourth guide 500 having an enclosed cylindrical aperture 522, and FIGS. 6B and 6C show a fourth guide 500' having a slot 524.

The fourth guide 500/500' attaches to the first guide 100. A fastener 512 is inserted through the fourth guide 500/500' and into one of the apertures 140 of the first guide 100. The fourth guide 500 has a medial extension portion 520.

The medial extension portion 520 of fourth guide 500 (FIG. 6A) defines an aperture 522 for receiving a fixation element 550 aligned with the first portion 60p and second portion 60d of the bone 60 after applying the corrective translation and rotation to the distal portion 60d. For example, a k-wire or nail 550 can be passed through the aperture 522 and can enter the proximal portion 60p and distal portion 60d of the bone 60. In some embodiments, as shown in FIG. 6A, the aperture 522 is a cylindrical hole with anterior and posterior entrances, and the fixation element (e.g., k-wire, olive wire, or the like) 550 is fed through the aperture 522, through the first portion 60p of the bone 60, and into the second portion 60d of the bone.

In other embodiments (as shown in FIG. 6C), the medial extension portion 520 of fourth guide 500' has a slot 524 for receiving the fixation element 550. The slot 524 extends from the lateral surface of the medial extension portion 522 to the interior (e.g., center) of the medial extension portion 522. The slot 524 is configured to permit quick removal of the fourth guide 500' from the first guide 100 and the fixation element 550, after the fixation element 550 is inserted through the first portion 60p of the bone 60 and into the second portion 60d of the bone.

Figure 7A:
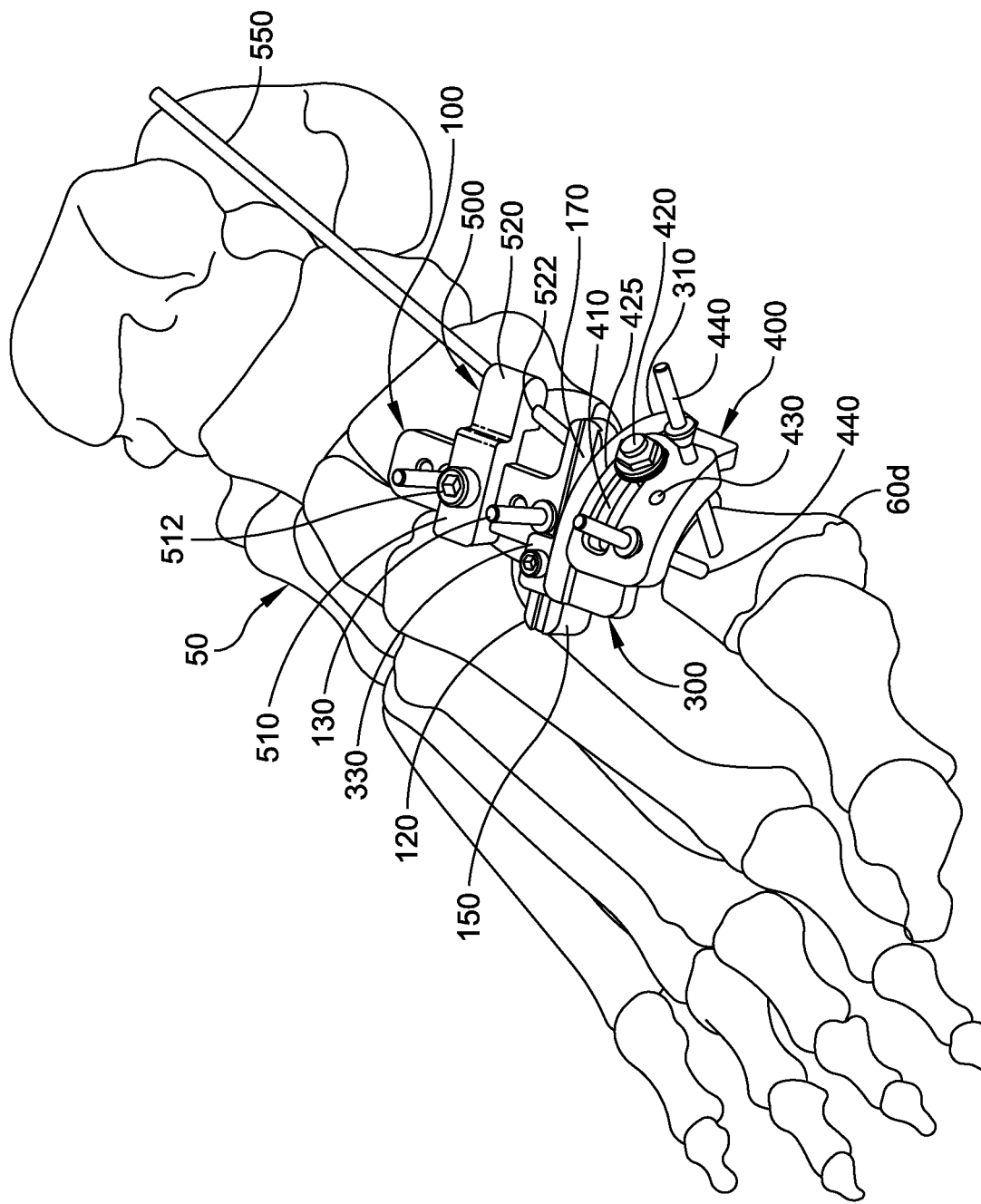
FIGS. 7A-7C are isometric, dorsal and medial views of the guidance system with a fixation device penetrating the fourth guide, proximal portion, and distal portion of first metatarsal.
Figure 7B:
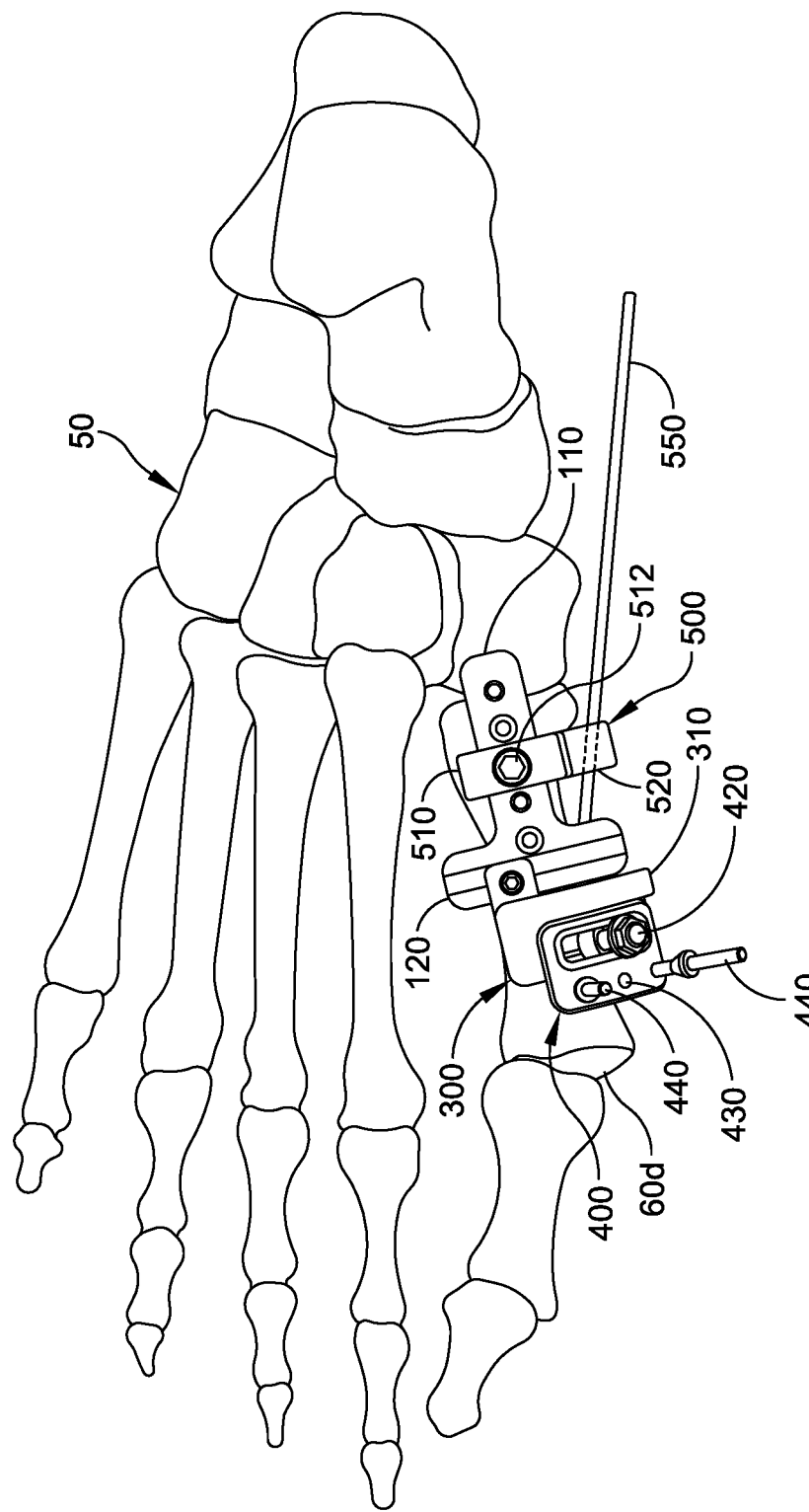
Figure 7C:
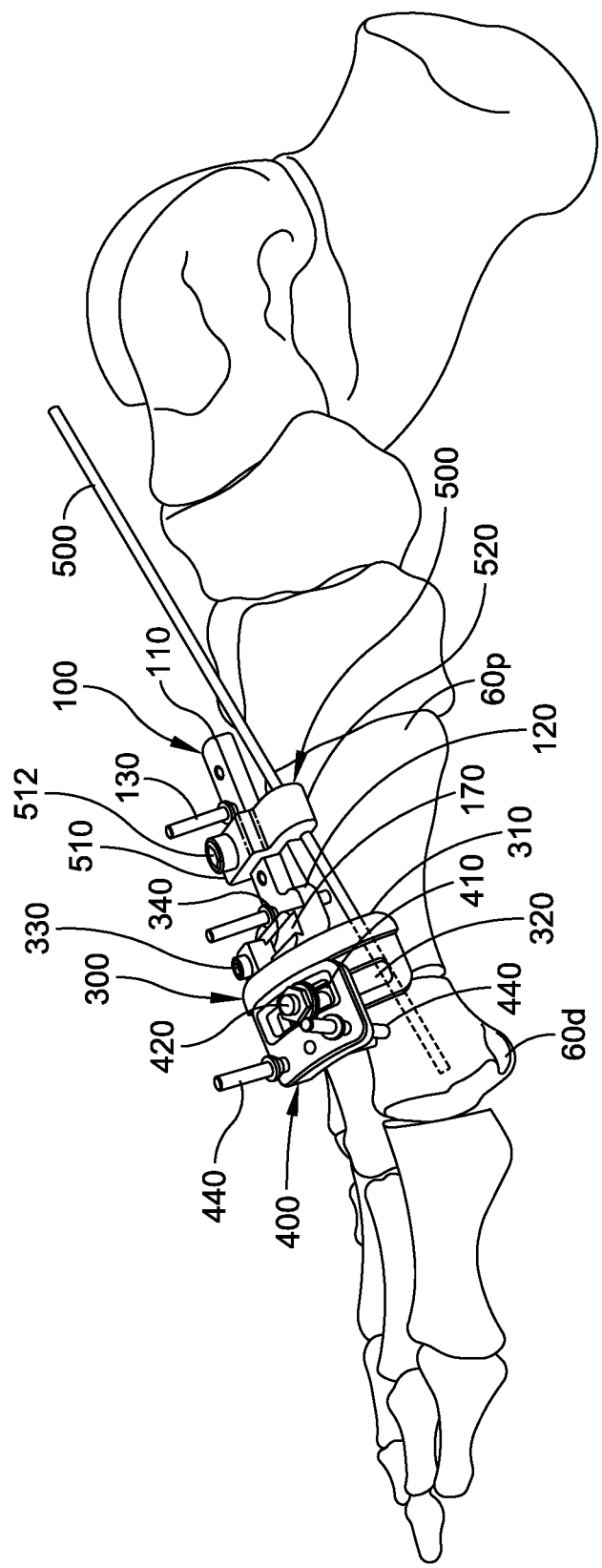

FIGS. 7A-7C show the configuration of the guidance system after the fixation element 550 has been inserted through the aperture 522 of the fourth guide 500 (or slot 524 of fourth guide 500'), through the first portion 60p of the bone 60, and into the second portion 60d of the bone. The fixation element 550 fixes the distal portion 60d in abutting relationship with the proximal portion 60p during the recovery from surgery.

Subsequently, to remove the fourth guide 500, the fastener 512 is removed. In the case of the medial extension portion 520 having an enclosed cylindrical aperture 522, the fourth guide 500 (of FIG. 6A) slides in the posterior direction over the fixation element 550.

In the case of the fourth guide 500' (FIG. 6C) having a slot 524 extending to the lateral surface of the medial extension portion 520, once the fastener 512 is removed, the fourth guide 500' can slide off of the fixation element 550 in the transverse (e.g., medial) direction, perpendicular to the axis of the fixation element 550. The slot 524 may allow the surgeon to remove the fourth guide 500' more quickly.

Once the fourth guide 500/500' is removed, the surgeon can put a cannulated drill over fixation element 550, insert a screw or nail in the proximal portion 60p and distal portion 60d of the bone.

In some embodiments, the first guide 100, second guide 300, third guide 400 and fourth guide 500/500' comprise a radiolucent material (e.g., polymer or aluminum), to allow the surgeon to insert and view a k-wire under fluoroscope from the dorsal side of the guidance system.

Figure 8:
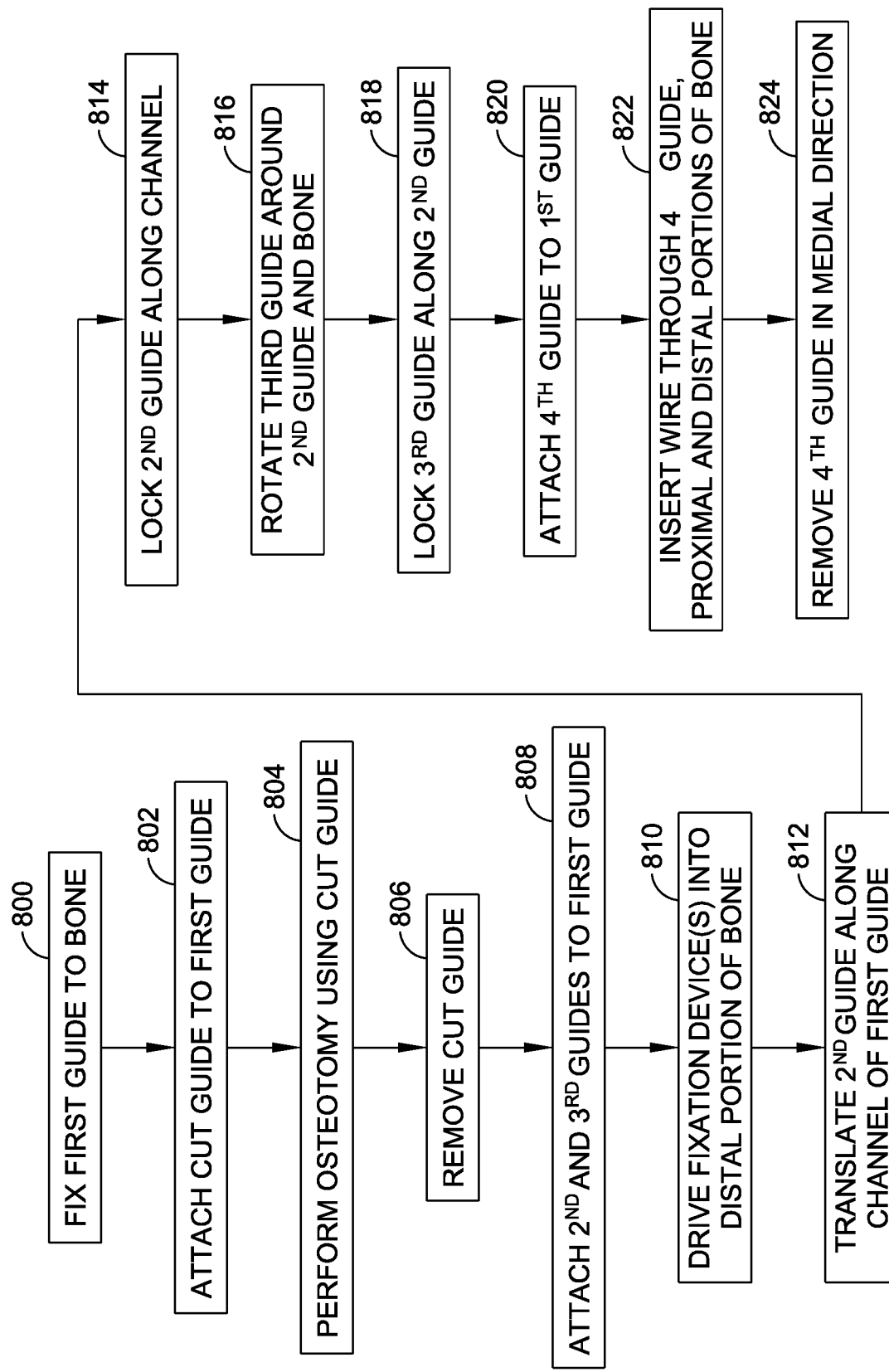
FIG. 8 is a flow chart of a method of using the guidance system.

FIG. 8 is a flow chart of an exemplary method of using the guidance system described above.

At step 800, the surgeon fixes the first guide 100 to the bone 60 (e.g., first metatarsal), so that the proximal portion 110 of the first guide is aligned with the central longitudinal axis of the bone.

At step 802, the surgeon attaches the cut guide 200 to the first guide 100. The attachment can be performed using pins and mating receptacles, a dovetail joint, or the like.

At step 804, the surgeon performs the osteotomy. For example, the surgeon can insert a burr in the slot 210 of the cut guide 200 and sweep the burr across the bone.

At step 806, the surgeon removes the cut guide 200 from the first guide 100.

At step 808, the surgeon attaches the subassembly comprising the second guide 300 and the third guide 400 to the first guide. For example, if the second guide has a rail and the first guide has a channel 170, the rail is inserted in the channel and translated along the length of the channel.

At step 810, the surgeon drives one or more fixation devices 440 (e.g., k-wire or olive wire) through apertures 430 in the third guide and into the distal portion 60d of the bone. The apertures 430 can align the fixation devices 440 along respective radii emanating from the center of curvature of the third guide 400.

At step 812, the surgeon translates the second guide (relative to the first guide) so the rail (not shown) moves within the channel 170, to correct the medial deviation of the bone.

At step 814, the surgeon locks the second guide relative to the first guide.

At step 816, the surgeon slides the third guide 400 over the second guide 300 in the tangential direction, causing the third guide to revolve around the central axis of the distal portion 60d of the bone 60, and rotating the distal portion 60d. The surgeon views the bone and guidance system by fluoroscopy, and determines that the rotational deviation of the bone is corrected when the sesamoids 61, 62 are in the plantar position. For example, if the surgeon is looking at a dorsal view, the sesamoids 61, 62 appear on the lateral side of the metatarsal before correction, and disappear from the dorsal view of the metatarsal when the rotation has been corrected.

At step 818, the surgeon locks the rotation of the third guide 400 relative to the second guide 300.

At step 820, the surgeon attaches the fourth guide 500 or 500' to the first guide 100.

At step 822, the surgeon inserts a fixation device (e.g., k-wire 550 or olive wire) through the aperture 522 of the fourth guide 500 (or the slot 524 of fourth guide 500'), the proximal portion 60p of the bone, and into the distal portion 60d of the bone.

At step 824, the surgeon removes the fourth guide 500/500' from the first guide 100. For example, if the fourth guide 500' is used, the surgeon can slide the fourth guide 500' off in the medial direction, so the wire 550 exits the fourth guide via the slot 524. Once the fourth guide 500' has been removed, the surgeon can insert a cannulated drill around the fixation device 550, enlarge the opening in the proximal portion 60p and distal portion 60d, and insert a screw or nail into the opening. Subsequently, after healing is completed, the fixation device 550, first guide 100, second guide 300 and third guide 400 can be removed. In other embodiments, the surgeon may remove the first guide 100, second guide 300 and third guide 400 prior to removal of the fixation device 550.

Although the subject matter has been described in terms of exemplary embodiments, it is not limited thereto. Rather, the appended claims should be construed broadly, to include other variants and embodiments, which may be made by those skilled in the art.

What is claimed is:

1. A guidance system for hallux valgus correction, comprising:
    a first guide configured to be detachably mounted to a first portion of a bone, the first guide having a first axis for alignment with a longitudinal axis of the first portion of the bone;
    a second guide mountable on the first guide, the second guide slidably translatable in a transverse direction relative to the first axis; and
    a third guide mountable on the second guide such that the third guide is translatable along a curved path extending at least part way around the longitudinal axis.

2. The guidance system for hallux valgus correction of claim 1, wherein the third guide has a lock for fixing a position of the third guide along the curved path.

3. The guidance system for hallux valgus correction of claim 2, wherein the lock comprises a threaded post or a spring loaded device.

4. The guidance system for hallux valgus correction of claim 2, wherein the lock comprises a threaded post, and further wherein the second and third guides include plates configured to receive the threaded post extending through respective slots in the second and third guides.

5. The guidance system for hallux valgus correction of claim 4, wherein the plates of the second and third guides further define at least one aperture for receiving a fixation element therethrough.

6. The guidance system for hallux valgus correction of claim 4, wherein the plate of the third guide is curved.

7. The guidance system for hallux valgus correction of claim 1, wherein the first guide has a first planar surface perpendicular to the first axis, and the second guide has a second planar surface arranged to slide in the transverse direction relative to the first planar surface.

8. The guidance system for hallux valgus correction of claim 1, further comprising a fourth guide attachable to the first guide, the fourth guide defining an aperture for receiving a fixation element aligned with a second portion of the bone.

9. The guidance system for hallux valgus correction of claim 8, wherein the fourth guide has a slot continuous with the aperture of the fourth guide, wherein the slot is configured for removal of the fourth guide from the first guide and the fixation element while the fixation element is inserted in the second portion of the bone.

10. The guidance system for hallux valgus correction of claim 1, further comprising a cut guide attachable to the first guide, the cut guide having a slot for receiving a cutting tool configured to separate a second portion of the bone from the first portion of the bone.

11. The guidance system for hallux valgus correction of claim 1, wherein:
    the first guide is a T-shaped member having apertures for receiving fixation elements and a planar surface, rail or channel for guiding the second guide;
    the second guide includes a plate configured to move in a tangential direction along the surface, rail or channel; and
    the third guide is a curved plate having a slot therethrough, the guidance system further comprising a threaded post or a spring loaded device extending through the slot of the third guide, for locking the third guide relative to the second guide.

* * * * *